(12) United States Patent
Ruff (10) Patent No.: US 9,717,880 B2
(45) Date of Patent: Aug. 1, 2017

(54) PERSONAL AIRWAY HUMIDIFICATION APPARATUS AND METHOD

(71) Applicant: William Henry Ruff, Valparaiso, IN (US)

(72) Inventor: William Henry Ruff, Valparaiso, IN (US)

( * ) Notice: Subject to any disclaimer, the term of this patent is extended or adjusted under 35 U.S.C. 154(b) by 409 days.

(21) Appl. No.: 13/776,423

(22) Filed: Feb. 25, 2013

(65) Prior Publication Data

US 2013/0220322 A1 Aug. 29, 2013

Related U.S. Application Data

(60) Provisional application No. 61/602,645, filed on Feb. 24, 2012.

(51) Int. Cl.
| | |
|---|---|
| *A61M 16/00* | (2006.01) |
| *A61M 16/16* | (2006.01) |
| *A61M 16/08* | (2006.01) |
| *A61M 16/20* | (2006.01) |
| *A61M 16/10* | (2006.01) |
| *A61M 16/04* | (2006.01) |

(52) U.S. Cl.
CPC ........ *A61M 16/16* (2013.01); *A61M 16/0057* (2013.01); *A61M 16/0488* (2013.01); *A61M 16/0875* (2013.01); *A61M 16/1075* (2013.01); *A61M 16/208* (2013.01); *A61M 2205/3368* (2013.01)

(58) Field of Classification Search
CPC .... A61M 16/16–16/168; A61M 16/20; A61M 16/208; A61M 15/00; A61M 15/0018; A61M 15/0021; A61M 11/00; A61M 11/001; A61M 11/02; A61M 11/04; A61M 11/041–11/048
See application file for complete search history.

(56) References Cited

U.S. PATENT DOCUMENTS

| | | | | |
|---|---|---|---|---|
| 1,939,134 | A * | 12/1933 | Peak | A61M 16/104 128/203.25 |
| 3,733,060 | A * | 5/1973 | Merritt | 261/1 |
| 4,243,396 | A * | 1/1981 | Cronenberg | A61M 11/06 128/203.16 |

(Continued)

*Primary Examiner* — Peter S Vasat
*Assistant Examiner* — Ned T Heffner
(74) *Attorney, Agent, or Firm* — Hartman Global IP Law; Gary M. Hartman; Domenica N. S. Hartman (57) ABSTRACT

A personal airway humidification apparatus includes means for generating a heated air laden with gaseous (molecular) water. The personal airway humidification apparatus further includes an accumulator coupled to the generating means for retaining a volume of the gaseous water-laden heated air prior to being delivered by natural breathing to a user and a delivery tube coupled to the accumulator. The delivery tube has a sufficiently large diameter bore to enable the user's natural breathing to draw the gaseous water-laden heated air from the accumulator and through the delivery tube. The personal airway humidification apparatus also includes a one-way valve coupled to the delivery tube for venting exhalations of the user to atmosphere and preventing the exhalations from being exhaled back into the delivery tube and an interface device by which the gaseous water-laden heated air enters the user's mouth from the delivery tube.

18 Claims, 7 Drawing Sheets

(56) References Cited

U.S. PATENT DOCUMENTS

| | | | |
|---|---|---|---|
| 4,708,831 A * | 11/1987 | Elsworth et al. ............. 261/130 |
| 5,148,801 A * | 9/1992 | Douwens et al. ....... 128/203.16 |
| 5,692,095 A | 11/1997 | Young |
| 5,870,525 A | 2/1999 | Young |
| 6,162,046 A | 12/2000 | Young et al. |
| 6,347,936 B1 | 2/2002 | Young et al. |
| 6,585,509 B2 | 7/2003 | Young et al. |
| 6,634,864 B1 | 10/2003 | Young et al. |
| 7,431,570 B2 | 10/2008 | Young et al. |
| 2007/0083677 A1 | 4/2007 | Cecka et al. |
| 2009/0220222 A1 | 9/2009 | Rabin et al. |
| 2009/0224064 A1 | 9/2009 | Brodbeck et al. |
| 2009/0324206 A1 | 12/2009 | Young et al. |
| 2010/0142934 A1 | 6/2010 | Sellers et al. |
| 2011/0210458 A1 | 9/2011 | Brodbeck et al. |
| 2015/0165146 A1 | 6/2015 | Bowman et al. |

* cited by examiner

PERSONAL AIRWAY HUMIDIFICATION APPARATUS AND METHOD

CROSS REFERENCE TO RELATED APPLICATIONS

This application claims the benefit of U.S. Provisional Application No. 61/602,645, filed Feb. 24, 2012, the contents of which are incorporated herein by reference.

BACKGROUND OF THE INVENTION

The present invention generally relates to devices and methods for airway humidification. More particularly, this invention relates to personal humidification devices adapted to provide heated, gaseous (molecular) water-laden air to a patient.

In the past, numerous devices have been developed for use as personal humidification devices. These devices have been used, for example, to specifically target promoting pulmonary hygiene (mucous mobilization and/or clearance) and bronchial dilation in a patient. U.S. Pat. No. 4,773,410 and devices manufactured by the OECO Corporation and Gulfstream, various aerosol-producing or nebulization devices, continuous positive airway pressure (CPAP) and biphasic positive airway pressure (BIPAP) devices manufactured by Respironics, Res-med, Fisher Paykel and others, and Vapotherm "High Flow" technology devices have been devised and employed to do a similar job. Various steam humidifiers and "facial saunas" are also known personal devices that are intended for short-term use. Room, steam or warm mist humidifiers are also known for use as room humidifiers, though these devices are not adapted for personal use, in other words, to treat an individual as opposed to treating the environment within a room. The literature involving the medical use of gaseous (molecular) water, as opposed to aerosols containing a suspension of microdroplets of water, and findings relating to such uses is voluminous.

Room humidifiers are not personal humidifiers by definition and/or use. To be used as personal humidification, one would need to position oneself over the exhaust area for prolonged periods of time. It is physically difficult to do this and makes it very difficult or nearly impossible to do other things at the same time. Room humidifiers are simply designed for other than personal airway support.

Personal humidification devices of the types disclosed by U.S. Pat. No. 4,773,410 and manufactured by the OECO Corporation and Gulfstream are fairly large heavy machines and employ pumps to force humidified air through small bore tubing and simple nasal cannulas. These devices are uniquely capable of providing humidification effectively and efficiently to a sleeping subject. They can, but need not, produce noise levels that may disturb the user and others nearby. The devices can be expensive to own and operate, and may require professional cleaning and maintenance.

CPAP, BIPAP, high-flow and blow-over technology devices tend to be light, quiet, portable and provide varying levels of humidification. However, these rarely provide 100% water-saturated gases. In addition, few of these devices employ heated delivery and fewer employ monitored heated delivery. All of these devises use high-flow, fan-driven technologies that use large bore tubing and very uncomfortable and clumsy face masks or cannulas. While designed for sleep use, these devices are the least comfortable and cannot compete for comfort with smallbore heat-monitored pump-driven equipment. Consequently, many patients spend thousands of dollars on home equipment of this type that they dislike or will not use. True compliance to prescribed use can be inconsistent at best.

Personal heated humidifiers are well suited for humidifying an individual's airway. These devices are typically small, portable and relatively inexpensive. The shortcoming of this technology is that these devices are adapted for short-term use only. These devices are typically designed for fifteen to thirty minute uses, and require the user to bend over the device throughout this period of time. As with room humidifying steamers, other activities are nearly impossible while using personal humidifiers.

Aerosol devices are small, portable and usually inexpensive. The problem with these devices is that they employ sub-droplet liquid phase water (nongaseous or molecular), which means that this technology can transport viruses and bacteria to the user. In addition, the inhalation of nebulized water can cause broncho-spasm. This technology can be used to transport medication, but its uses for other treatment purposes have been questioned. Medically-supervised use may be advisable due to increased risk of broncho-spasms and potential for bacterial and/or viral inoculation, and therefore aerosol devices are not necessarily prescribed for personal humidification performed at home.

Accordingly, there is an ongoing need for personal humidification devices capable of being safely used by individuals at home that allow users some degree of freedom and comfort during use.

BRIEF DESCRIPTION OF THE INVENTION

The present invention provides a method and device suitable for safely providing heated, gaseous (molecular) water-laden air to an individual in a manner capable of promoting pulmonary hygiene and bronchial dilation, while also allowing the individual some degree of freedom during its use.

According to a first aspect of the invention, a personal airway humidification apparatus includes means for generating a heated air laden with gaseous (molecular) water. The personal airway humidification apparatus further includes an accumulator coupled to the generating means for retaining a volume of the gaseous water-laden heated air prior to being delivered by natural breathing to a user and a delivery tube coupled to the accumulator. The delivery tube has a sufficiently large diameter bore to enable the user's natural breathing to draw the gaseous water-laden heated air from the accumulator and through the delivery tube. The personal airway humidification apparatus also includes a one-way valve coupled to the delivery tube for venting exhalations of the user to atmosphere and preventing the exhalations from being exhaled back into the delivery tube and an interface device by which the gaseous water-laden heated air enters the user's mouth from the delivery tube.

According to a second aspect of the invention, a personal airway humidification process includes generating a heated air laden with gaseous (molecular) water, retaining a volume of the gaseous water-laden heated air in an accumulator, and using natural breathing by a user to draw the gaseous water-laden heated air from the accumulator to the user.

According to a third aspect of the invention, an apparatus for adapting a room humidifier for use as a personal humidifier includes means for coupling the apparatus to the outlet of the room humidifier, an accumulator for retaining a volume of the gaseous water-laden heated air prior to being delivered by natural breathing to a user, and a delivery tube coupled to the accumulator. The delivery tube has a sufficiently large diameter bore to enable the user's natural breathing to draw the gaseous water-laden heated air from the accumulator and through the delivery tube. The apparatus further includes a one-way valve coupled to the delivery tube for venting exhalations of the user to atmosphere and preventing the exhalations from being exhaled back into the delivery tube and an interface device by which the gaseous water-laden heated air enters the user's mouth from the delivery tube.

A technical effect of the invention is the ability to provide users with humidified air in a comfortable manner. In particular, it is believed that, by delivering gaseous water-laden heated air to a user by the natural breathing of the user, the user will be more comfortable and, therefore, more likely to be able to sleep or perform various tasks while using the personal airway humidification apparatus.

Other aspects and advantages of this invention will be better appreciated from the following detailed description.

DETAILED DESCRIPTION OF THE INVENTION

The present invention provides a personal airway humidification apparatus and method capable of delivering a heated gaseous (molecular) water-laden air to a user. The apparatus can be configured to be comfortable and safe for use in the user's home, and adapted for use whether the user is awake, asleep, or unconscious. The invention provides hydration to airways of the user, particularly for the purpose of promoting pulmonary hygiene and bronchial dilation.

Figure 1:
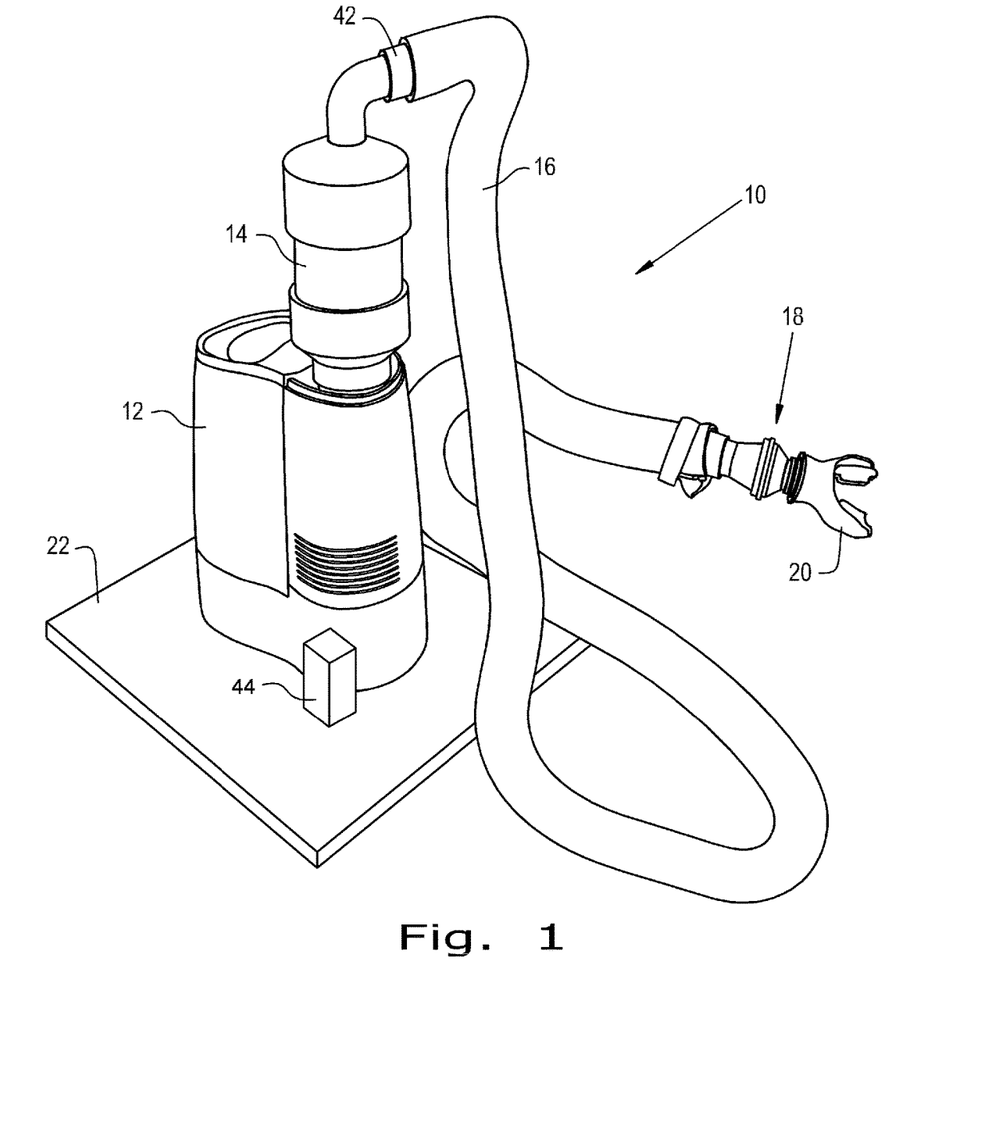
FIG. 1 shows a personal airway humidification apparatus that utilizes a commercially-available warm-mist room humidifier that produces heated gaseous (molecular) water in accordance with an embodiment of the invention.
Figure 2:
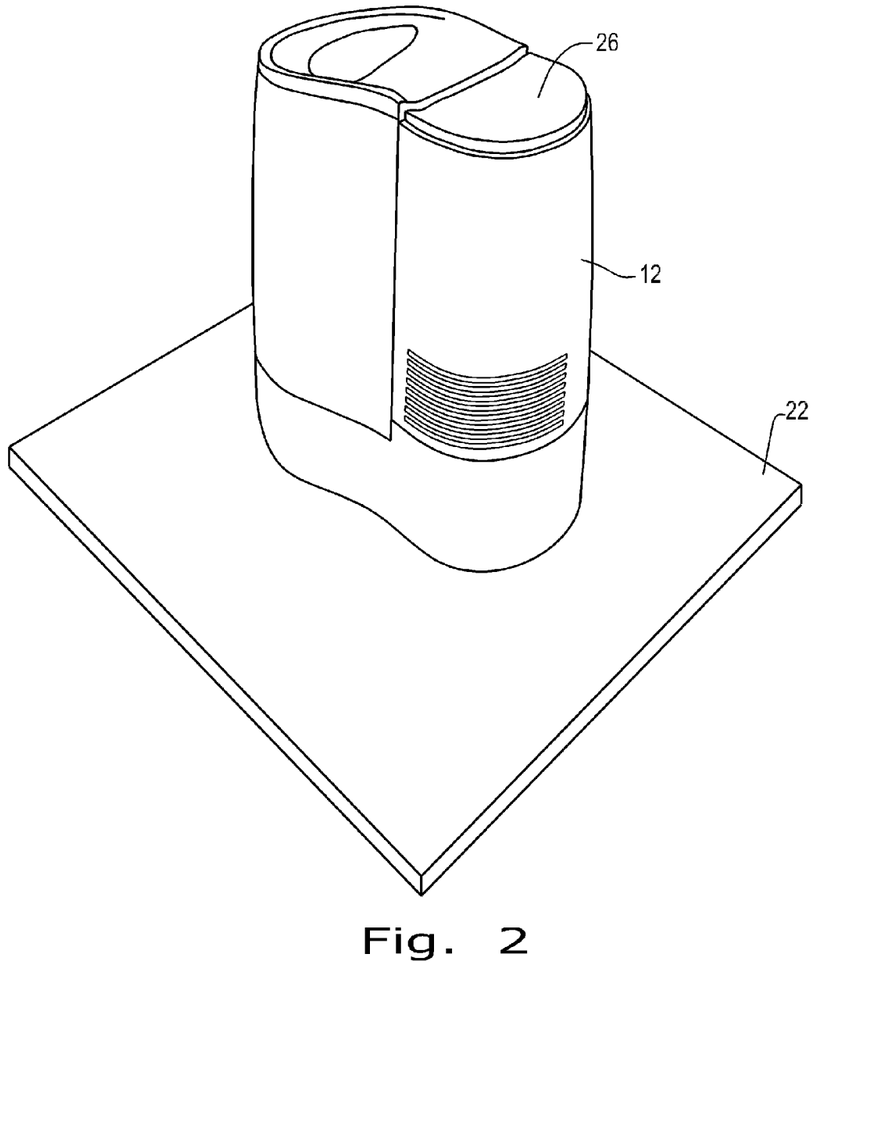
FIG. 2 is an isolated view of the warm-mist humidifier of FIG. 1.

FIG. 1 represents a personal airway humidification apparatus 10 in accordance with a nonlimiting embodiment of the invention. As represented, the apparatus 10 comprises a humidifier 12, an accumulator 14, an insulated hose assembly 16 comprising a delivery tube 38 (FIG. 5), a valve 18, and a mouth piece 20. The humidifier 12 can be a commercially-available warm-mist room humidifier capable of delivering heated air laden with gaseous (molecular) water. Although it is foreseeable that a fan or pump 44 may be coupled to the apparatus 10 to gently promote the flow of the gaseous water-laden heated air through the apparatus 10 to the user, the apparatus 10 preferably does not require a forced flow, but instead can rely on the natural buoyance resulting from the air being heated to rise from the humidifier 12 into the accumulator 14. Suitable humidifiers 12 produce about 100% water-saturated air, and preferably 100% water-saturated air, at a given temperature. The humidifiers 12 produce air at a temperature of at least about 86° F. (30° C.), but below that which would cause discomfort to the user, and may be adjusted over the temperature range. In FIGS. 1 and 2, the humidifier 12 is represented as being secured to a base 22 to prevent tipping. The humidifier 12 may be secured to the base 22 by any known means, for example, by an elastic strap, bolts, or clamps.

Figure 3:
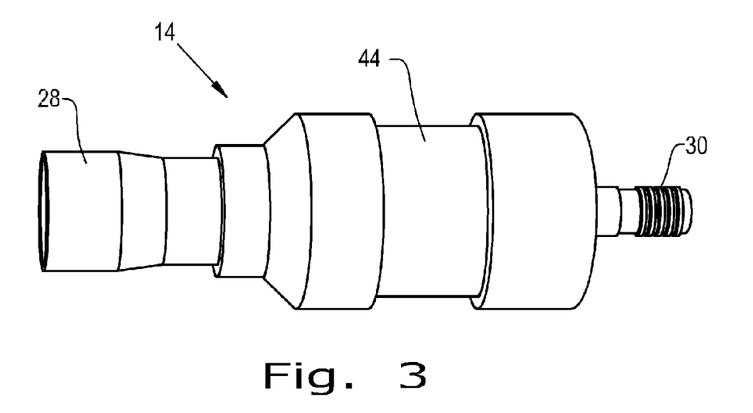
FIG. 3 is an isolated view of an accumulator shown in FIG. 1 as receiving the heated gaseous water from the warm-mist humidifier.

The apparatus 10 is represented in FIG. 1 as utilizing the accumulator 14 or other suitable retention volume for the gaseous water-laden heated air prior to being delivered to a user by the natural breathing of the user. FIG. 3 is an isolated view of an exemplary accumulator 14 defining reservoir 44 whose volume per unit length is greater than the delivery tube 38. The reservoir 44 of the accumulator 14 may have any capacity as long as the accumulator 14 provides a sufficient volume of retained gaseous water-laden heated air for inhalation during a user's natural breathing.

One end 28 of the accumulator 14 is specifically tailored to couple with an outlet 26 of the humidifier 12 (FIG. 2). Attached to an opposite end 30 of the accumulator 14 is one end of the insulated hose assembly 16, shown in isolation in FIG. 4. The hose assembly 16 comprises a delivery tube 38 that can be insulated in any suitable manner, such as with an insulative cloth cover 32 to minimize heat loss to the surroundings. Additionally, the delivery tube 38 may be heated. The delivery tube 38 can be of various types known in the medical industry. A nonlimiting example of such a delivery tube 38 is shown in FIG. 5. The delivery tube 38 has a sufficiently large diameter bore to enable the user's natural breathing to draw the gaseous water-laden heated air from the accumulator 14 and through the delivery tube 38 and accommodate all inspiration needs with the warm humidified atmosphere. The combined volume of air within the humidifier 12, the accumulator 14, and the delivery tube 38 must be larger than the capacity of the patient's lungs to allow the user to comfortably inhale.

Figure 4:
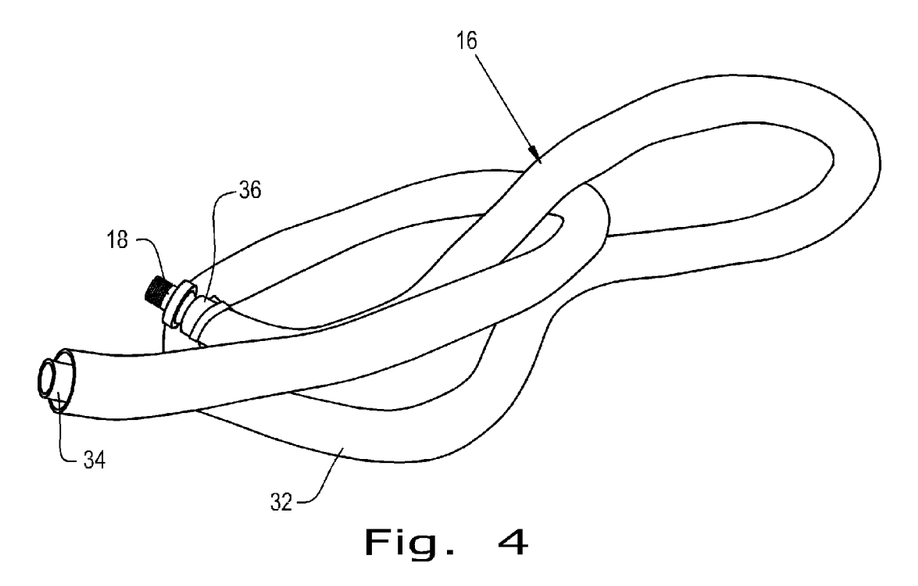
FIG. 4 is an isolated view of an insulated hose shown in FIG. 1 as receiving the heated gaseous water from the accumulator.
Figure 5:
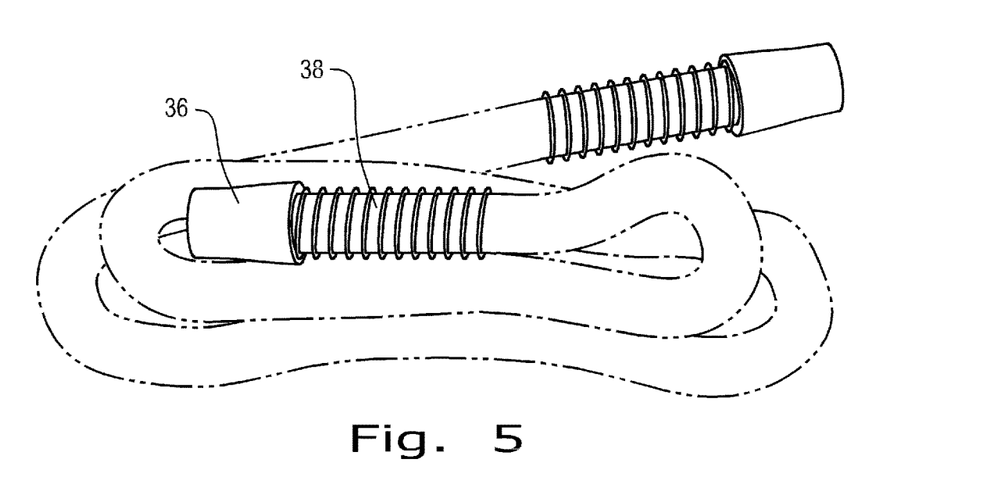
FIG. 5 is an isolated view of a commercially-available delivery hose of a type used in CPAP and BIPAP devices, and which can be insulated as shown in FIG. 4 for use as the insulated hose in FIGS. 1 and 4.
Figure 6:
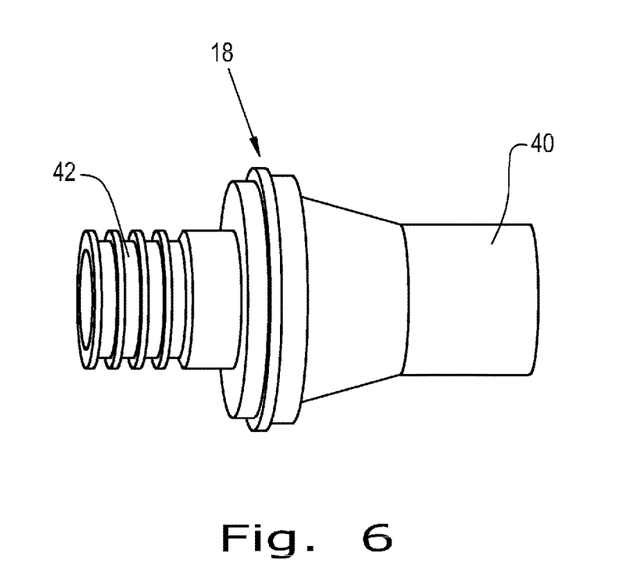
FIG. 6 is an isolated view of a commercially-available check valve of a type that can be installed on the insulated hose as shown in FIG. 4.
Figure 9:
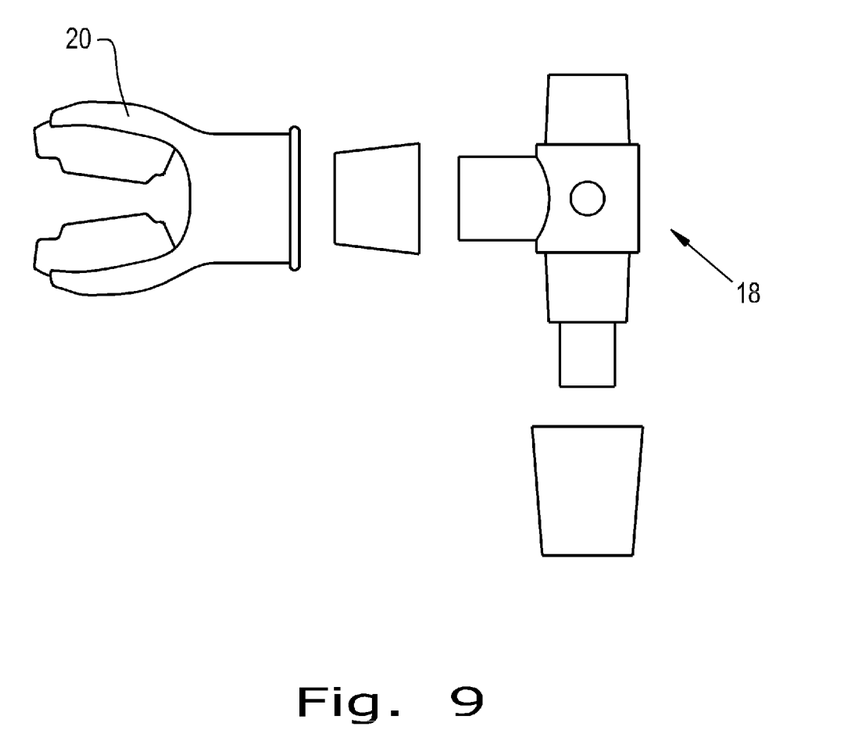
FIG. 9 is an isolated view of a commercially-available double check valve of a type that can be installed on the insulated hose of FIG. 4.

As seen in FIG. 4, one end 36 of the delivery tube 38 is coupled to a portion 40 of the valve 18, which is preferably a one-way (check) double valve to eliminate the dead space in the delivery tube 38 caused by its length, such that exhalations are vented to atmosphere instead of being exhaled back into the delivery tube 38. Preferably, the valve 18 is a double valve as represented in FIG. 9.

In combination, the humidifier 12, accumulator 14 and insulated hose assembly 16 cooperate to deliver to the user 100% humidified air at a temperature of at least about 86° F. (30° C.), but below that which would cause discomfort to the user. Sensors (not shown) may be utilized within the delivery tube 38 to monitor the temperature and/or dew point of the humidified air being delivered to the user, as well as the temperature and/or dew point of the user's exhalation.

Figure 7:
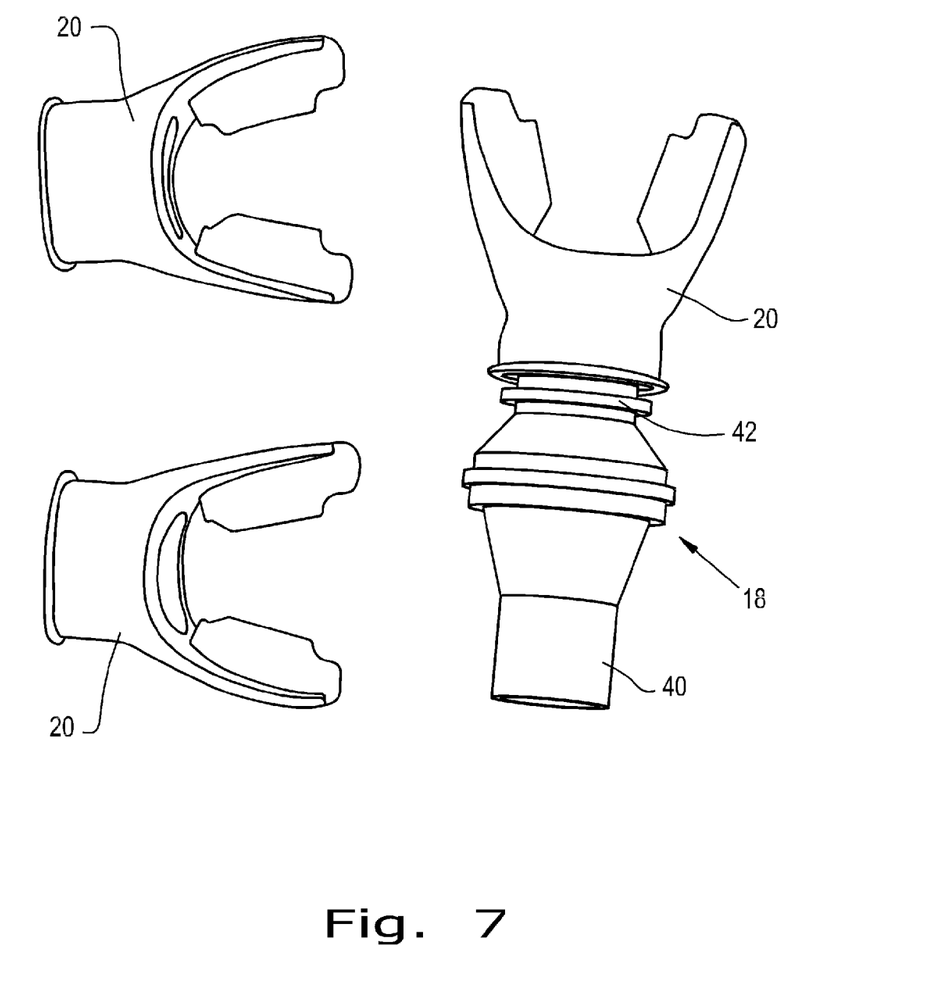
FIG. 7 shows examples of commercially-available mouthpieces of types that can be used with the warm-mist humidifier of FIG. 1, and shows one of the mouthpieces assembled with the check valve of FIG. 6.
Figure 8:
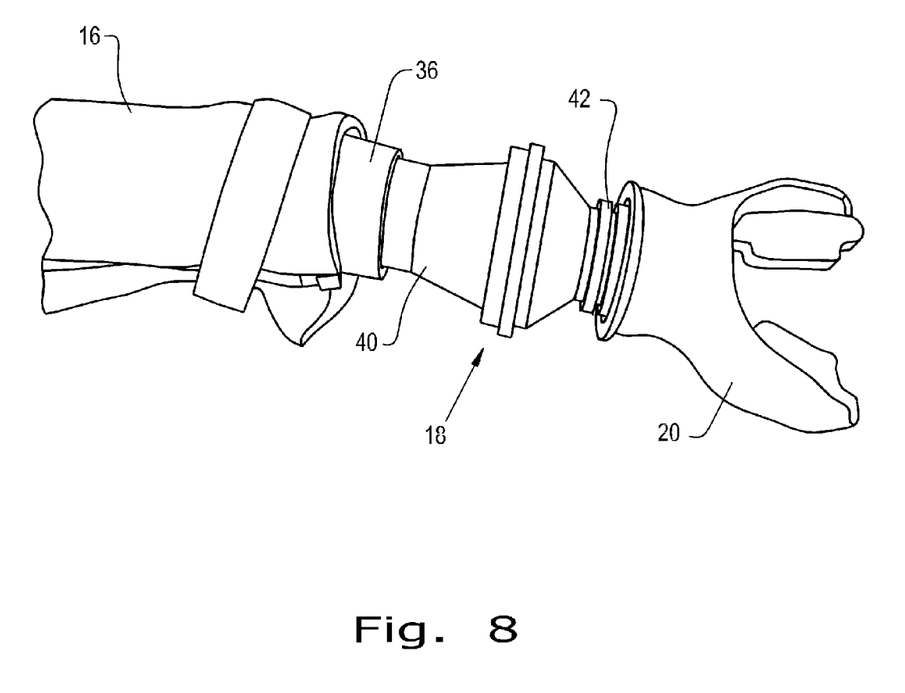
FIG. 8 shows the mouthpiece and check valve assembly of FIG. 7 installed on the insulated hose of FIG. 4.

The invention can employ any suitable interface 20 by which the gaseous water-laden heated air enters the user's mouth, and preferably the interface 20 does not cover portions of the face other than the mouth and nose areas. The interface 20 should provide direct access for the air to the user's mouth and/or nose rather than to the general area of the face. Allowing the heated air to contact other areas of the user's face can be uncomfortable for the user. Furthermore, the interface 20 preferably is adapted be used while the user is able to engage in relatively stationary activities. As evident from FIGS. 7 and 8, mouthpieces of snorkels are nonlimiting examples of suitable interfaces 20. The apparatus 10 can be equipped with multiple mouthpieces to permit its use by multiple users. The interface 20 may be adapted to connect directly to a complementary fitting 42 of the valve 18, as represented in FIGS. 7, 8, and 9.

In combination, the components of the apparatus 10 enable the apparatus 10 to be used while the user is awake or unconscious. Furthermore, the apparatus 10 is suitable for use as a personal humidifier over long periods of time to heal a damaged airway of the user (such as caused by dehydration from breathing the earth's common atmosphere, or continuous exposure to air conditioning, or any other atmosphere that is cooler and/or drier than the airway). The apparatus 10 can also be used postoperatively to temporarily reduce thirst and warm a hypothermal condition. The apparatus 10 may be adapted to promote relieving of bronchospasms, mucus retention, and the discomfort of the common cold or sore throat.

As noted above, the user's natural breathing is preferably the mechanism that drives the airway humidification performed by the apparatus 10. As represented in the FIG. 1, the accumulator 14 is preferably located above the humidifier 12 to promote the gaseous water-laden heated air to rise naturally into the accumulator 14 without the use of a fan or pump. Such an arrangement ensures that the main driving force pulling air from the accumulator 14 towards the mouthpiece is the natural breathing of the user. Relying on the natural breathing of the user is believed to be more comfortable for the user during use relative to systems that forcibly pump air into the user's lungs. This will make it easier for the user to sleep or perform various tasks while using the personal airway humidification apparatus 10.

The heated gaseous (molecular)water protects the user's airway from the stress of heating, hydrating and filtering what would otherwise be cool, dry atmospheric air, and allows the user to breathe a humidified atmosphere that is compatible with the airway and lungs. Because the gaseous water-laden heated air reduces stress on the airway by performing the warming and humidification tasks normally performed by a healthy airway, it is believed that the apparatus 10 promotes natural support of a damaged airway that could cause respiratory distress or even lung pathology in the user. Mucus clearance is rapid, easy, passive and very safe. Furthermore, it is believed that humidification performed by the apparatus 10 may provide a natural bronchial dilator capable of naturally preventing asthmatic episodes.

It is a well-known and acknowledged concept that breathing plays a role in systemic fluid balance, chemical balance and temperature control. As one controls the temperature of the inspired atmosphere, body temperature reactions can be quickly experienced. A common complaint of the elderly is the feeling of being cold. Inhalation of the gaseous water-laden heated air provided by the apparatus 10 of this invention may provide an easy, comfortable, controllable and safe remedy. With the above described invention, users can avail themselves of a healthy alternative to normal atmospheric conditions.

While the invention has been described in terms of specific embodiments, it is apparent that other forms could be adopted by one skilled in the art. For example, the physical configuration of the apparatus 10 could differ from that shown, and materials and processes other than those noted could be used. Furthermore, it is within the scope of the invention that the apparatus could be modified to include a fan or pump capable of promoting the flow and, consequently, the user's inhalation of the gaseous water-laden heated air. Therefore, the scope of the invention is to be limited only by the following claims.

The invention claimed is:

1. A personal airway humidification apparatus comprising:
    generating means comprising a humidifier that draws atmospheric air therein and heats and humidifies the atmospheric air to deliver through an outlet of the humidifier a gaseous water-laden heated air consisting of heated air and gaseous (molecular) water;
    an accumulator coupled to the humidifier and defining a retention volume therein for collecting a retained volume of the gaseous water-laden heated air prior to being delivered by natural breathing to a user, the accumulator having an accumulator inlet located so that all flow of the gaseous water-laden heated air from the outlet of the humidifier to the accumulator inlet is rising, the accumulator having an accumulator outlet for the retained volume of the gaseous water-laden heated air within the retention volume, the accumulator outlet being located above the accumulator inlet so that the accumulator outlet receives the gaseous water-laden heated air rising vertically from the accumulator inlet, the retention volume of the accumulator being entirely above the outlet of the humidifier so that the retained volume of the gaseous water-laden heated air within the accumulator is entirely above the outlet of the humidifier;
    a delivery tube coupled to the accumulator outlet, the delivery tube having a sufficiently large diameter bore to enable the user's natural breathing to draw from the accumulator and through the delivery tube the gaseous water-laden heated air collected in the accumulator;
    a one-way valve coupled to the delivery tube for venting exhalations of the user to atmosphere and preventing the exhalations from being exhaled back into the delivery tube; and
    an interface device configured for delivering the gaseous water-laden heated air from the delivery tube directly into the mouth and/or nose of the user;
    wherein the retention volume of the accumulator defines a reservoir whose volume per unit length is greater than the delivery tube and the reservoir collects and accumulates a sufficient volume of the gaseous water-laden heated air for inhalation during a user's natural breathing; and
    wherein the gaseous water-laden heated air generated by the humidifier is 100% water-saturated air and the personal airway humidification apparatus and the accumulator, delivery tube, and interface device thereof are configured so that the user receives the 100% water-saturated air through the interface device at a temperature of at least about 30° C.

2. The personal airway humidification apparatus of claim 1, the generating means further comprising a fan or pump coupled thereto to promote the flow of the gaseous water-laden heated air from the humidifier to the accumulator.

3. The personal airway humidification apparatus of claim 1, wherein operation of the apparatus is by:
    continuous flow of the gaseous water-laden heated air from the humidifier into the accumulator by natural buoyancy and not forced flow by the apparatus; and the user drawing the gaseous water-laden heated air from the accumulator by natural inhalation and not forced flow by the apparatus.

4. The personal airway humidification apparatus of claim 1, wherein the interface device is a mouthpiece configured for directly delivering the gaseous water-laden heated air to the user's mouth.

5. The personal airway humidification apparatus of claim 1, wherein the delivery tube is insulated to inhibit heat loss from the gaseous water-laden heated air within the delivery tube.

6. The personal airway humidification apparatus of claim 1, further comprising sensors within the delivery tube adapted to monitor the temperature and/or dew point of the gaseous water-laden heated air being delivered to the user and/or the temperature and/or dew point of the user's exhalation.

7. The personal airway humidification apparatus of claim 1, wherein the accumulator is separate from the generating means, the accumulator comprising means for physically coupling the accumulator to the outlet of the humidifier.

8. The personal airway humidification apparatus of claim 1, wherein the gaseous water-laden heated air exits the humidifier by flowing vertically through the outlet of the humidifier.

9. The personal airway humidification apparatus of claim 1, wherein the accumulator inlet is located above the outlet of the humidifier so that the accumulator inlet receives the gaseous water-laden heated air that rises vertically from the outlet of the humidifier caused solely by natural buoyancy of the gaseous water-laden heated air.

10. The personal airway humidification apparatus of claim 1, wherein the accumulator outlet is located above the accumulator inlet so that the accumulator outlet receives the gaseous water-laden heated air that rises vertically from the accumulator inlet.

11. The personal airway humidification apparatus of claim 1, wherein the accumulator outlet is located above the accumulator inlet and the retention volume of the accumulator is entirely above the outlet of the humidifier so that the retained volume of the gaseous water-laden heated air within the accumulator is entirely above the outlet of the humidifier and rises vertically through the retention volume.

12. The personal airway humidification apparatus of claim 1, wherein the humidifier is a room humidifier.

13. The personal airway humidification apparatus of claim 12, wherein the coupling means, the accumulator, the delivery tube, the one-way valve, and the interface device constitute an apparatus for adapting the room humidifier for use as a personal airway humidifier.

14. The personal airway humidification apparatus of claim 13, further comprising a fan or pump for forcing the gaseous water-laden heated air from the room humidifier to the accumulator.

15. The personal airway humidification apparatus of claim 13, wherein operation of the apparatus is by:
continuous flow of the gaseous water-laden heated air from the humidifier into the accumulator by natural buoyancy and not forced flow by the apparatus; and
the user drawing the gaseous water-laden heated air from the accumulator by natural inhalation and not forced flow by the apparatus.

16. The personal airway humidification apparatus of claim 13, wherein the interface device is a mouthpiece configured for directly delivering the gaseous water-laden heated air to the user's mouth.

17. The personal airway humidification apparatus of claim 13, wherein the delivery tube is insulated to inhibit heat loss from the gaseous water-laden heated air within the delivery tube.

18. The personal airway humidification apparatus of claim 13, further comprising sensors within the delivery tube adapted to monitor the temperature and/or dew point of the humidified air being delivered to the user and/or the temperature and/or dew point of the user's exhalation.

* * * * *